(12) United States Patent
Avalle et al.

(10) Patent No.: US 7,893,081 B2
(45) Date of Patent: *Feb. 22, 2011

(54) TYROSINE KINASE INHIBITORS

(75) Inventors: Paolo Avalle, Hertford (GB); Jennifer R. Foley, Garwood, NJ (US); Peter Mullens, Welwyn Garden City (GB); Yaling Wang, Westfield, NJ (US); Peter Yehl, Cranbury, NJ (US)

(73) Assignee: Merck & Co., Inc., Rahway, NJ (US)

( * ) Notice: Subject to any disclaimer, the term of this patent is extended or adjusted under 35 U.S.C. 154(b) by 16 days.

This patent is subject to a terminal disclaimer.

(21) Appl. No.: 12/316,868

(22) Filed: Dec. 17, 2008

(65) Prior Publication Data

US 2009/0182002 A1    Jul. 16, 2009

Related U.S. Application Data

(60) Provisional application No. 61/008,614, filed on Dec. 20, 2007.

(51) Int. Cl.
*A01N 43/42* (2006.01)
*A61K 31/44* (2006.01)
*C07D 221/00* (2006.01)

(52) U.S. Cl. .................................... 514/290; 546/93

(58) Field of Classification Search ................ 514/290; 546/93

See application file for complete search history.

(56) References Cited

FOREIGN PATENT DOCUMENTS

| WO | WO 03/084931 | 10/2003 |
|---|---|---|
| WO | WO 2004/058742 | 7/2004 |
| WO | WO 2007/002254 | 1/2007 |
| WO | WO 2007002258 A2 * | 1/2007 |
| WO | WO 2007/050380 | 5/2007 |
| WO | WO 2007/050383 | 5/2007 |
| WO | WO 2007/050401 | 5/2007 |
| WO | WO 2008/008310 | 1/2008 |

OTHER PUBLICATIONS

Ma, PC et al. Cancer Research, vol. 65, No. 4, pp. 1479-1488 (2005), Functional expression and mutations of c-Met and its therapeutic inhibition with SU11274 and small interfering RNA in non-small cell lung cancer.
Ma, PC et al. Cancer Research, vol. 63, pp. 6272-6281 (2003), "c-MET mutational analysis in small cell lung cancer: novel juxtamembrane domain mutations regulating cytoskeletal functions".
Christensen, JG et al., Cancer Research., vol. 63, pp. 7345-7355 (2003), "A selective small molecule inhibitor of c-Met kinase inhibits c-Met-dependent phenotypes in vitro and exhibits cytoreductive antitumor activity in vivo".
Sattler, M et al., Cancer Research, vol. 63, pp. 5462-5469 (2003), "A novel small molecule Met inhibitor induces apoptosis in cells transformed by the oncogenic TPR-MET tyrosine kinase".
Christensen, JG et al., Cancer Letters, vol. 225, pp. 1-26 (2005), "c-Met as a target for human cancer and characterization of inhibitors for therapeutic intervention".
Puri, N et al., Cancer Research, vol. 67, No. 8, pp. 3529-3534 (2007), "A selective small molecule inhibitor of c-Met, PHA665752, inhibits tumorigenicity and angiogenesis in mouse lung cancer xenografts".
Zou, HY et al., Cancer Research, vol. 67, No. 9, pp. 4408-4417 (2007), "An orally available small-molecule inhibitor of c-Met, PF-2341066, exhibits cytoreductive antitumor efficacy through antiproliferative and antiangiogenic mechanisms".
Cassinelli, G et al., Molecular Cancer Therapeutics, vol. 5, No. 9, pp. 2388-2397 (2006), "Inhibition of c-Met and prevention of spontaneous metastatic spreading by the 2-indolinone RPI-1".
Martens, T et al., Clinical Cancer Research, vol. 12, No. 20, pp. 6144-6152 (2006), "A novel one-armed anti-c-Met antibody inhibits glioblastoma growth in vivo".
Ross, R et al., Poster B249, 2007 AARC-NCI-EORTC International Conference on Molecular Targets and Cancer Therapeutics, Oct. 2007, "A Phase 2 Study of the Dual MET/VEGFR2 Inhibitor XL880 in Patients (pts) with Papillary Renal Carcinoma (PRC)".
Office Communication from the USPTO mailed Apr. 28, 2008 with a three-month reply due of Jul. 28, 2008.
Amendment and Response dated Jun. 4, 2008 in reply to the Office Action mailed Apr. 28, 2008 from the USPTO.
Office Communication from the USPTO mailed Jul. 29, 2008 with a three-month reply due of Oct. 29, 2008.
Amendment and Response dated Sep. 5, 2008 in reply to the Office Action mailed Jul. 29, 2008 from the USPTO.
Notice of Allowance and Fees due Communication from the USPTO mailed Dec. 1, 2008 with a three-month reply due of Mar. 1, 2009.
Assignment Recordal with Recordation Cover Sheet faxed to USPTO on Feb. 23, 2009.
Issue Fee Transmittal faxed to USPTO on Feb. 25, 2009.

\* cited by examiner

*Primary Examiner*—Sreeni Padmanabhan
*Assistant Examiner*—Samira Jean-Louis
(74) *Attorney, Agent, or Firm*—David A. Muthard

(57) ABSTRACT

This invention relates to salt forms of the compound N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide, an inhibitor of tyrosine kinases, in particular the receptor tyrosine kinase MET, that are useful in the treatment of cellular proliferative diseases, for example cancer, hyperplasias, restenosis, cardiac hypertrophy, immune disorders and inflammation. In particular, the invention relates to the sodium salt of N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide.

2 Claims, 2 Drawing Sheets

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Glu Gln Glu Asp Glu Pro Glu Gly Asp Tyr Phe Glu Trp Leu Glu
1               5                   10                  15

TYROSINE KINASE INHIBITORS

CROSS REFERENCE TO RELATED APPLICATIONS

This application claims the benefit of U.S. Provisional Application No. 61/008,614, filed Dec. 20, 2007.

BACKGROUND OF THE INVENTION

This invention relates to salt forms of the compound N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide, an inhibitor of tyrosine kinases, in particular the receptor tyrosine kinase MET, that are useful in the treatment of cellular proliferative diseases, for example cancer, hyperplasias, restenosis, cardiac hypertrophy, immune disorders and inflammation. In particular, the invention relates to the sodium salt of N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide.

Recently, members of the MET proto-oncogene family, a subfamily of receptor tyrosine kinases, have drawn special attention to the association between invasion and metastasis. The MET family, including MET (also referred to as c-Met) and RON receptors, can function as oncogenes like most tyrosine kinases. MET has been shown to be overexpressed and/or mutated in a variety of malignancies. A number of MET activating mutations, many of which are located in the tyrosine kinase domain, have been detected in various solid tumors and have been implicated in invasion and metastasis of tumor cells.

The c-Met proto-oncogene encodes the MET receptor tyrosine kinase. The MET receptor is a 190 kDa glycosylated dimeric complex composed of a 50 kDa alpha chain disulfide-linked to a 145 kDa beta chain. The alpha chain is found extracellularly while the beta chain contains extracellular, transmembrane and cytosolic domains. MET is synthesized as a precursor and is proteolytically cleaved to yield mature alpha and beta subunits. It displays structural similarities to semaphoring and plexins, a ligand-receptor family that is involved in cell-cell interaction.

It is known that stimulation of MET via hepatocyte growth factor (also known as scatter factor, HGF/SF) results in a plethora of biological and biochemical effects in the cell. Activation of c-Met signaling can lead to a wide array of cellular responses including proliferation, survival, angiogenesis, wound healing, tissue regeneration, scattering, motility, invasion and branching morphogenesis. HGF/MET signaling also plays a major role in the invasive growth that is found in most tissues, including cartilage, bone, blood vessels, and neurons.

Various c-Met mutations have been well described in multiple solid tumors and some hematologic malignancies. The prototypic c-Met mutation examples are seen in hereditary and sporadic human papillary renal carcinoma (Schmidt, L. et al., *Nat. Tenet.* 1997, 16, 68-73; Jeffers, M. et al., *Proc. Nat. Acad. Sci.* 1997, 94, 11445-11500). Other reported examples of c-Met mutations include ovarian cancer, childhood hepatocellular carcinoma, metastatic head and neck squamous cell carcinomas and gastric cancers. HGF/MET has been shown to inhibit anoikis, suspension-induced programmed cell death (apoptosis), in head and neck squamous cell carcinoma cells.

MET signaling is implicated in various cancers, especially renal. The nexus between MET and colorectal cancer has also been established. In addition, when compared to the primary tumor, 70% of colorectal cancer liver metastasis showed MET overexpression. MET is also implicated in glioblastoma. Glioma MET expression correlates with glioma grade, and an analysis of human tumor specimens showed that malignant gliomas have a 7-fold higher HGF content than low-grade gliomas. Multiple studies have demonstrated that human gliomas frequently co-express HGF and MET and that high levels of expression are associated with malignant progression. It was further shown that HGF-MET is able to activate Akt and protect glioma cell lines from apoptotic death, both in vitro and in vivo.

RON shares a similar structure, biochemical features, and biological properties with MET. Studies have shown RON overexpression in a significant fraction of breast carcinomas and colorectal adenocarcinomas, but not in normal breast epithelia or benign lesions. Cross-linking experiments have shown that RON and MET form a non-covalent complex on the cell surface and cooperate in intracellular signaling. RON and MET genes are significantly co-expressed in ovarian cancer cell motility and invasiveness. This suggests that co-expression of these two related receptors might confer a selective advantage to ovarian carcinoma cells during either tumor onset or progression.

A number of reviews on MET and its function as an oncogene have recently been published: *Cancer and Metastasis Review* 22:309-325 (2003); *Nature Reviews/Molecular Cell Biology* 4:915-925 (2003); *Nature Reviews/Cancer* 2:289-300 (2002).

Since dysregulation of the HGF/MET signaling has been implicated as a factor in tumorgenesis and disease progression in many tumors, different strategies for therapeutic inhibition of this important RTK molecule should be investigated. Specific small molecule inhibitors against HGF/MET signaling and against RON/MET signaling have important therapeutic value for the treatment of cancers in which Met activity contributes to the invasive/metastatic phenotype.

SUMMARY OF THE INVENTION

The present invention relates to salt forms of the compound of formula I, that are useful for treating cellular proliferative diseases, for treating disorders associated with MET activity, and for inhibiting the receptor tyrosine kinase MET. The salt forms of the instant invention exhibit greater aqueous solubility than Compound I.

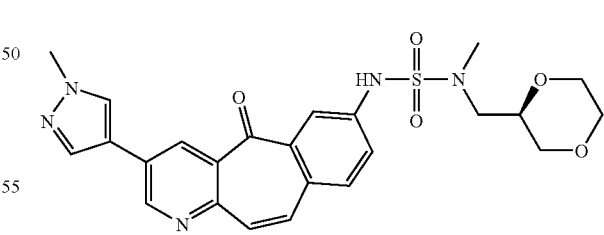

DETAILED DESCRIPTION OF THE INVENTION

Figure 1:
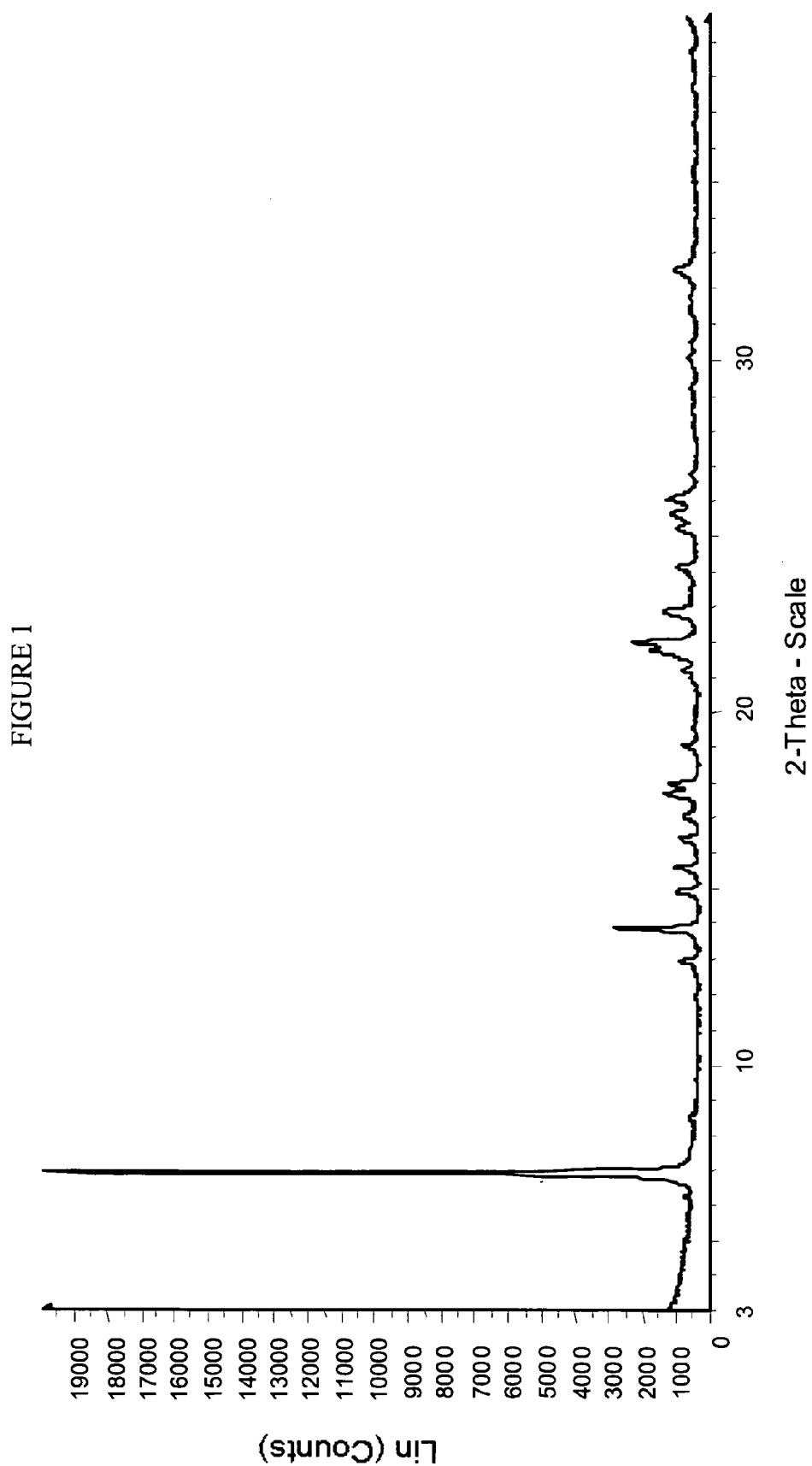
FIG. 1: The XRPD spectrum for N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide sodium salt dihydrate is shown.

The compounds of this invention are useful in the inhibition of tyrosine kinases, in particular the receptor tyrosine kinase MET, and are illustrated by a compound of Formula Ia:

Ia

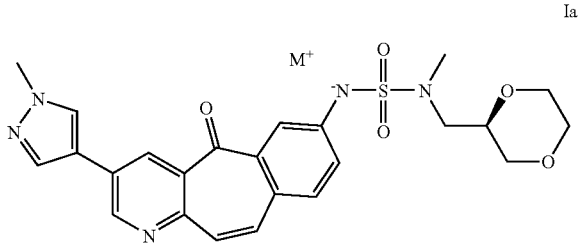

wherein M is selected from sodium, potassium, calcium, lithium, magnesium, zinc, tetraalkyl ammonium, tetraaryl ammonium, trialkylaryl ammonium, dialkyldiaryl ammonium, trialkylalkenyl ammonium, trialkyl ammonium and ammonium containing heterocyclyl wherein the alkyl, aryl, alkenyl and heterocyclyl are independently unsubstituted or substituted with a group selected from hydroxyl, alkoxyl and carboxylate.

In an embodiment of the invention, M is selected from sodium and potassium.

Specific examples of the compounds of the instant invention include:

N-[(2R)-1,4-dioxan-2-ylmethyl]-N-methyl-NA-[3-(1-methyl-1H-pyrazol-4-yl)-5-oxo-5H-benzo[4,5]cyclohepta[1,2-b]pyridin-7-yl]sulfamide sodium salt dihydrate; and N-[(2R)-1,4-dioxan-2-ylmethyl]-N-methyl-A'-[3-(1-methyl-1H-pyrazol-4-yl)-5-oxo-5H-benzo[4,5]cyclohepta[1,2-b]pyridin-7-yl]sulfamide potassium salt monohydrate.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198;

Showell, G. A. et al. Bioorganic & Medicinal Chemistry Letters (2006) 16:2555-2558).

When any variable (e.g. $R^7$, $R^8$, $R^b$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases another embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "alkyl" specifically includes methyl, ethyl, n-propyl, i-propyl, n-butyl, t-butyl, i-butyl, pentyl, hexyl, heptyl, octyl, nonyl, decyl, and so on.

The term "alkylene" means a hydrocarbon diradical group having the specified number of carbon atoms. For example, "alkylene" includes —$CH_2$—, —$CH_2CH_2$— and the like.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. For the purposes of this invention, the term "heterocyclic" is also considered to be synonymous with the terms "heterocycle" and "heterocyclyl" and is understood as also having the definitions set forth herein. "Heterocyclyl" therefore includes the above mentioned heteroaryls, as well as dihydro and tetrahydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, the term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" in this embodiment therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In another embodiment, heterocycle is selected from 2-azepinone, benzimidazolyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl.

The term "ammonium containing heterocyclyl" as used herein is intended to mean an nitrogen containing heterocyclyl that is a cation as a result of protonation or substitution on the nitrogen. Such ammonium containing heterocyclyls include protonated forms of N-ethylmorpholine, N-ethylpiperidine, morpholine, piperazine, piperidine, and the like.

As appreciated by those of skill in the art, "halo" or "halogen" as used herein is intended to include chloro, fluoro, bromo and iodo.

The alkyl, alkenyl, alkynyl, cycloalkyl, aryl, heteroaryl and heterocyclyl substituents may be substituted or unsubstituted, unless specifically defined otherwise. For example, a $(C_1-C_6)$ alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition:

—C(=O)CH$_2$CH(OH)CH$_3$, —(C=O)OH, —CH$_2$(OH)CH$_2$CH(O), and so on.

The preparation of pharmaceutically acceptable salts is generally described by Berg et al., "Pharmaceutical Salts," *J. Pharm. Sci.*, 1977:66:1-19.

Certain abbreviations, used in the Schemes and Examples, are defined below:

| | |
|---|---|
| APCI | Atmospheric pressure chemical ionization |
| DMF | Dimethylformamide |
| DMSO | Dimethyl sulfoxide |
| EtOAc | Ethyl acetate |
| LCMS | Liquid chromatographic mass spectrometry |
| MPLC | Medium pressure liquid chromatography |
| NBS | N-bromosuccinamide |
| TFA | Trifluoroacetic acid |
| TFAA | Trifluoroacetic anhydride |

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of Formula I hereinabove.

Schemes

As shown in Scheme A, reaction of a suitably substituted 2-methylnicotinate A-1 with strong base followed by reaction with a suitably substituted bromobenzaldehyde provides the olefin intermediate A-2. Subsequent polyphosphoric acid mediated cyclization provides the intermediate of the invention A-3.

Scheme B illustrates the use of intermediate A-3 in the preparation of compounds having a variety of amine and sulfide substituents.

Scheme C illustrates the incorporation of $R^1$ by a Suzuki coupling of an appropriately substituted boronic acid or boronic ester with the chloride of the fused pyridyl ring of the instant compounds.

Scheme D illustrates an alternative procedure for forming the tricyclic ring system of the instant compounds. Thus a suitably substituted nicotinoyl chloride D-1 is converted to intermediate D-2, which reacts with a suitably substituted boronic acid to provide the benzaldehyde D-3. Intermediate D-3 can then undergo base mediated cyclization to provide the compound D-4.
Scheme E illustrates generally the synthesis of the salts of the instant invention.
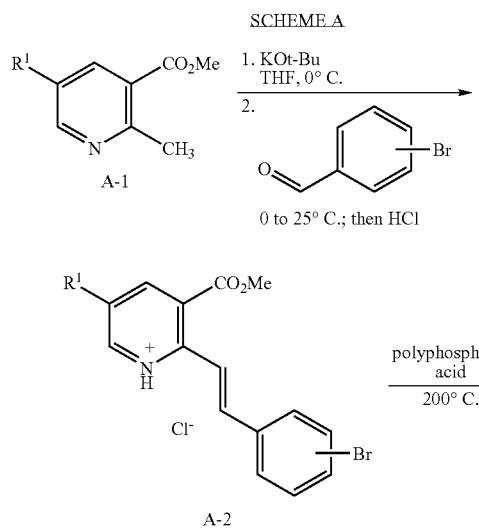
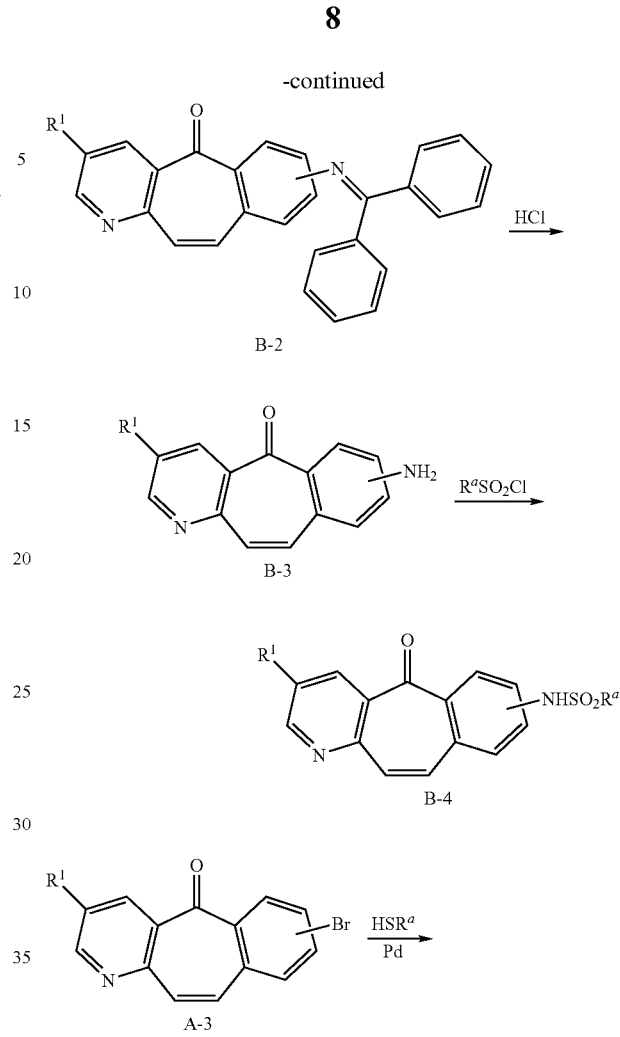

-continued
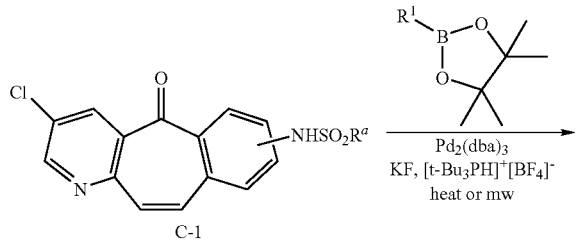
C-1
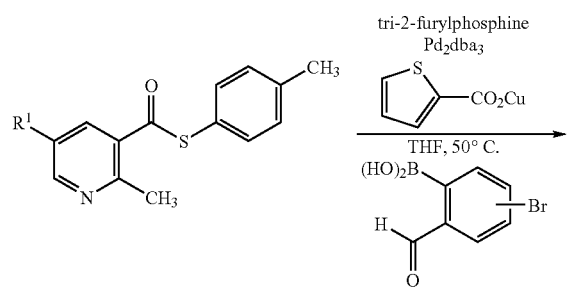
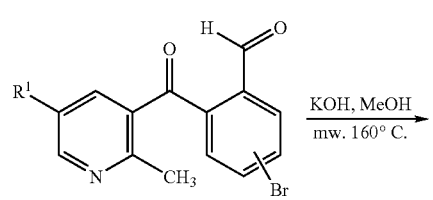
D-3
SCHEME D
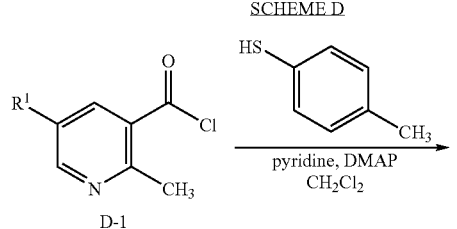
D-1
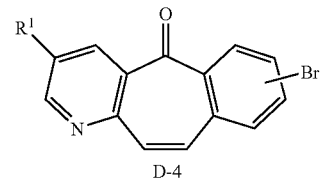
D-4
SCHEME E
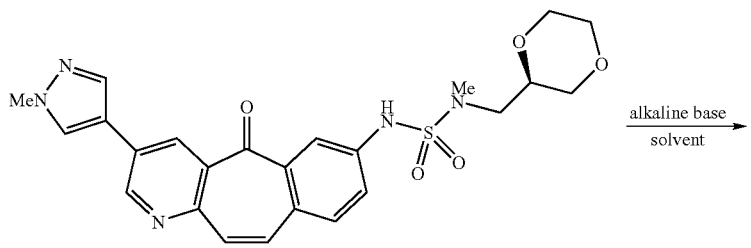
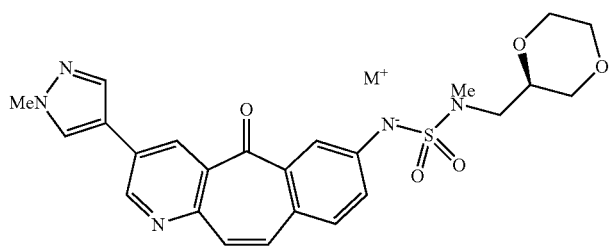

Utilities

The compounds of the invention are useful to bind to and/or modulate the activity of a tyrosine kinase, in particular, a receptor tyrosine kinase. In an embodiment, the receptor tyrosine kinase is a member of the MET subfamily. In a further embodiment, the MET is human MET, although the activity of receptor tyrosine kinases from other organisms may also be modulated by the compounds of the present invention. In this context, modulate means either increasing or decreasing kinase activity of MET. In an embodiment, the compounds of the instant invention inhibit the kinase activity of MET.

The compounds of the invention find use in a variety of applications. As will be appreciated by those skilled in the art, the kinase activity of MET may be modulated in a variety of ways; that is, one can affect the phosphorylation/activation of MET either by modulating the initial phosphorylation of the protein or by modulating the autophosphorylation of the other active sites of the protein. Alternatively, the kinase activity of MET may be modulated by affecting the binding of a substrate of MET phosphorylation.

The compounds of the invention are used to treat or prevent cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds, compositions and methods provided herein are particularly deemed useful for the treatment and prevention of cancer including solid tumors such as skin, breast, brain, cervical carcinomas, testicular carcinomas, etc. In an embodiment, the instant compounds are useful for treating cancer. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, non-small cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), rectal, colorectal and colon; Genitourinary tract: kidney (adenocarcinoma, Wilm's tumor [nephroblastoma], lymphoma, leukemia, papillary renal carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematolopic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, head and neck squamous cell carcinomas, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions. In another embodiment, the compounds of the instant invention are useful for treating or preventing cancer selected from: head and neck squamous cell carcinoma, histiocytic lymphoma, lung adenocarcinoma, small cell lung cancer, non-small cell lung cancer, pancreatic cancer, papillary renal carcinoma, liver cancer, gastric cancer, colon cancer, multiple myeloma, glioblastoma and breast carcinoma. In still another embodiment, the compounds of the instant invention are useful for treating cancer selected from: histiocytic lymphoma, lung adenocarcinoma, small cell lung cancer, pancreatic cancer, liver cancer, gastric cancer, colon cancer, multiple myeloma, glioblastoma and breast carcinoma. In yet another embodiment, the compounds of the instant invention are useful for treating cancer selected from: ovarian cancer, childhood hepatocellular carcinoma, metastatic head and neck squamous cell carcinomas, gastric cancer, breast cancer, colorectal cancer, cervical cancer, lung cancer, nasopharyngeal cancer, pancreatic cancer, glioblastoma and sarcoma In another embodiment, the compounds of the instant invention are useful for the prevention or modulation of the metastases of cancer cells and cancer. In particular, the compounds of the instant invention are useful to prevent or modulate the metastases of ovarian cancer, childhood hepatocellular carcinoma, metastatic head and neck squamous cell carcinomas, gastric cancers, breast cancer, colorectal cancer, cervical cancer, lung cancer, nasopharyngeal cancer, pancreatic cancer, glioblastoma and sarcomas.

The compounds of this invention may be administered to mammals, such as humans, either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

For example, compounds of the instant invention can be administered in a total daily dose of up to 1000 mg. Compounds of the instant invention can be administered once daily (QD), or divided into multiple daily doses such as twice daily (BID), and three times daily (TID). Compounds of the instant invention can be administered at a total daily dosage of up to 1000 mg, e.g., 200 mg, 300 mg, 400 mg, 600 mg, 800 mg or 1000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

The instant compounds are also useful in combination with known therapeutic agents and anti-cancer agents. For example, instant compounds are useful in combination with known anti-cancer agents. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, and an apoptosis inducing agent.

And another embodiment of the invention is a method of treating cancer that comprises administering a therapeutically effective amount of a compound of Formula I in combination with one or more of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®V); cladribine (Leustatin®, 2-CdA®); clofarabine (Clolar®); cyclophosphamide (Cytoxan®&, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®V); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®V); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); and zoledronate (Zometa®).

And yet another embodiment of the invention is a method of treating cancer that comprises administering a therapeutically effective amount of a compound of Formula I in combination with paclitaxel or trastuzumab.

The instant invention also includes a pharmaceutical composition useful for treating or preventing cancer that comprises a therapeutically effective amount of a compound of Formula I and a compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonists; an inhibitor of cell proliferation and survival signaling, an agent that interfers with a cell cycle checkpoint, and an apoptosis inducing agent.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

These and other aspects of the invention will be apparent from the teachings contained herein.

Assays

The compounds of the instant invention described in the Examples were tested by the assays described below and were found to have MET inhibitory activity. Other assays are known in the literature and could be readily performed by those of skill in the art (see, for example, U.S. Patent Application Publications US 2005/0075340 A1, Apr. 7, 2005, pages 18-19; and PCT Publication WO 2005/028475, Mar. 31, 2005, pages 236-248).

I. In Vitro Kinase Assays

Recombinant GST-tagged cytosolic domains of human c-Met and other receptor tyrosine kinases including mouse c-Met, human Ron, KDR, IGFR, EGFR, FGFR, Mer, TrkA and Tie2 are used to determine whether the compounds of the instant invention modulate the enzymatic activities of these kinases.

Soluble recombinant GST-tagged cytosolic domains of c-Met and other receptor tyrosine kinases are expressed in a baculovirus system (Pharmingen) according to a protocol recommended by the manufacturer. The c-DNA encoding each cytosolic domain is subcloned into a baculovirus expression vector (pGcGHLT-A, B or C, Pharmingen) containing an in frame 6× histidine tag and a GST tag. The resulting plasmid construct and BaculoGold baculovirus DNA (Pharmingen) are used to co-transfect Sf9 or Sf21 insect cells. After confirming expression of GST-tagged kinase fusion, a high titer recombinant baculovirus stock is produced, expression conditions are optimized, and a scaled up expression of rat KDR-GST fusion is performed. The fusion kinase is then purified from the insect cell lysate by affinity chromatography using glutathione agarose (Pharmingen). The purified protein is dialyzed against 50% glycerol, 2 mM DTT, 506 mM Tris-HCl (pH 7.4) and stored at −20° C. The protein concentrations of the fusion proteins are determined using Coomassie Plus Protein Assay (Pierce) with BSA as standard.

The kinase activities of c-Met and other kinases are measured using a modified version of the homogeneous time-resolved tyrosine kinase assay described by Park et al. (1999, *Anal. Biochem.* 269:94-104).

The procedure for determining the potency of a compound to inhibit c-Met kinase comprises the following steps:

1. Prepare 3-fold serial diluted compound solutions in 100% dimethyl sulfoxide (DMSO) at 20× of the desired final concentrations in a 96 well plate.
2. Prepare a master reaction mix containing 6.67 mM $MgCl_2$, 133.3 mM NaCl, 66.7 mM Tris-HCl (pH 7.4), 0.13 mg/ml BSA, 2.67 mM dithiothreitol, 0.27 nM recombinant c-Met and 666.7 nM biotinylated synthetic peptide substrate (biotin-ahx-EQEDEPEGDYFEWLE-CONH$_2$) (SEQ. ID. NO.:1).
3. In a black assay plate, add 2.5 µl of compound solution (or DMSO) and 37.5 µl of master reaction mix per well. Initiate the kinase reaction by adding 10 µl of 0.25 mM MgATP per well. Allow the reactions to proceed for 80 min at room temperature. The final conditions for the reaction are 0.2 nM c-Met, 0.5 µM substrate, 50 µM MgATP, 5 mM $MgCl_2$, 100 mM NaCl, 2 mM DTT, 0.1 mg/ml BSA, 50 mM Tris (pH 7.4) and 5% DMSO.
4. Stop the kinase reaction with 50 µl of Stop/Detection buffer containing 10 mM EDTA, 25 mM HEPES, 0.1% TRITON X-100, 0.126 µg/ml Eu-chelate labeled anti-phosphotyrosine antibody PY20 (cat. # AD0067, PerkinElmer) and 45 µg/ml Streptavidin-allophycocyanin conjugate (cat. # PJ25S, Prozyme).
5. Read HTRF signals on a Victor reader (PerkinElmer) in HTRF mode after 60 min.
6. $IC_{50}$ is determined by fitting the observed relationship between compound concentration and HTRF signal with a 4-parameter logistic equation.

Essentially the same procedure was used to determine the potency of compounds to inhibit mouse c-Met, human Ron, KDR, IGFR, EGFR, FGFR, Mer, TrkA and Tie2 except that the concentration of enzyme varied in individual assays (0.2 nM mouse c-Met; 2.5 nM Ron, 8 nM KDR; 0.24 nM IGFR; 0.24 nM EGFR; 0.14 nM FGFR; 16 nM Mer; 8 nM TrkA; 8 nM Tie2).

The Compound 1 in the Examples was tested in the above assay and found to have an $IC_{50} \geq 50$ µM.

II. Cell Based-c-Met Autophosphorylation Assay

A sandwich ELISA assay is used to assess MET autophosphorylation in MKN45 gastric cancer cells, in which MET is constitutively activated. Briefly a monolayer of cells was pre-treated with compounds or the vehicle and then lysed. The MET in a cell lysate was captured by an anti-MET antibody immobilized on a plastic surface. A generic anti-phosphotyrosine antibody or one of several specific anti-phospho-MET antibodies is then allowed to bind captured MET and is detected using HRP-conjugated secondary antibody. The procedure for determining the potency of a compound to inhibit MET autophosphorylation in MKN45 cells comprises the following steps:

Day 1

1. Coat a 96-well ELISA plate overnight at 4° C. with 100 µl/well of 1 µg/ml capture antibody solution (Af276, R&D).
2. Seed a separate 96-well culture plate with MKN45 cells at 90,000 cells/well in 0.1 ml of growth media (RPMI 1640, 10% FBS, 100 ug/mL Pen-Strep, 100 ug/mL L-glutamine, and 10 mM HEPES) and culture overnight at 37° C./5% $CO_2$ to 80-90% confluence.

Day 2
1. Wash the ELISA plate 4× with 200 μl/well of wash buffer (TBST+0.25% BSA). Incubate the ELISA plate with 200 μl/well of blocking buffer (TBST+1.5% BSA) for 3-5 hrs at RT.
2. Prepare a half-long dilution series of 200× compound in DMSO. Dilute the series to 10× with assay media (RPMI 1640, 10% FBS, and 10 mM HEPES).
3. Add 10× compound solutions (11 μl/well) to the culture plate containing MKN45 cells. Incubate the plate at 37° C./5% $CO_2$ for 60 min.
4. Lyse the cells with 100 μl/well of lysis buffer (30 mM Tris, pH 7.5, 5 mM EDTA, 50 mM NaCl, 30 mM sodium pyrophosphate, 50 mM NaF, 0.5 mM $Na_3VO_4$, 0.25 mM potassium bisperoxo(1,10-phenanthroline)-oxovanadate, 0.5% NP40, 1% Triton X-100, 10% glycerol, and a protease inhibitor cocktail) at 4° C. for 90 min.
5. Remove blocking buffer from the ELISA plate, wash the plate 4× with 200 μl/well of wash buffer. Transfer 90 μl/well of MKN45 cell lysate from the culture plate to the ELISA plate. Incubate sealed assay plate at 4° C. with gentle shaking overnight.

Day 3
1. Wash the ELISA plates 4 times with 200 μl/well wash buffer.
2. Incubate with 100 μl/well primary detection antibody (1 μg/ml in TBST+1% BSA) for 1.5 hours at ambient temperature. The following primary antibodies have been used: 4G10 from UpState, anti-pMet(1349) and anti-pMet(1369), both from Biosource.
3. Wash the ELISA plates 4 times with wash buffer. Add 100 μl/well of secondary antibody (1:1000 anti-mouse IgG-HRP diluted in TBST+1% BSA for 4G10, or 1:1000 anti-rabbit IgG-HRP for anti-pMet(1349) and anti-pMet(1365)). Incubate at room temperature with gentle mixing for 1.5 hours. Wash 4× with 200 ul/well wash buffer.
4. Add 100 μl/well of Quanta Blu reagent (Pierce) and incubate at room temperature for 8 minutes. Read fluorescence (Excitation wavelength: 314 nm, emission wavelength: 425 nm) on a Spectramax Gemini EM plate reader (Molecular Devices).
5. $IC_{50}$ is calculated by fitting the relationship between compound concentration and fluorescence signal with a 4-parameter logistic equation.

III. MKN45 Cell Proliferation/Viability Assay

MKN45 human gastric cancer cells are known to overexpress constitutively activated c-Met. siRNA-mediated partial knock down of c-Met was found to induce pronounced growth inhibition and apoptosis in MKN45 cells, suggesting a vital role of c-Met in this cell line. The assay described here measures the effect of c-Met inhibitors on proliferation/viability of MKN45 cells. The procedure for determining the potency of a compound to inhibit MKN45 proliferation/viability comprises the following steps.

On day 1, plate MKN45 cells at 3000 cells/95 μl medium (RPMI/10% FCS, 100 mM HEPES, penicillin and streptomycin) per well in a 96 well plate. Maintain the plate in an incubator at 37° C./5% $CO_2$. Prepare 3-fold serial diluted compound solutions at 1000× of desired final concentrations in DMSO.

On day 2, prepare 50× compound solutions by diluting the 1000× compound solutions with the medium. Add 5 μl 20× compound solution per well to the MKN45 cell culture described above. Return the plate to the incubator.

On day 5, add 50 μl lysis buffer (ViaLight Reagents Kit, Catalog No. LT07-221, Cambrex): per well. Lyse the cells at room temperature for 15 minutes. Then add 50 μl detection reagent (ViaLight Reagents Kit) and incubate for 3 minutes. The plate is read on a TOPCOUNT (PerkinElmer) in luminescence mode. $IC_{50}$ is calculated by fitting the relationship between compound concentration and luminescence signal with a 4-parameter logistic equation.

IV. HGF-Induced Cell Migration Assay

The HGF-induced migration of HPAF pancreatic cancer cells was assessed using BD Falcon Fluoroblock 96-Multiwell Insert plates (Cat # 351164, BD Discovery Labware). The plate consists of wells each of which is partitioned by a micro-porous membrane into the top and bottom chambers. Pancreatic cancer cells are plated on the top side of the membrane and migrate to the underside of the membrane in response to chemo-attractant added to the lower chamber. The cells on the under side of the membrane are labeled with a fluorescent dye and detected by a fluorescence plate reader. The procedure for determining the potency of a compound to inhibit cell migration comprises the following steps.
1. Prepare test compound solutions of 1000× final concentrations in 100% DMSO
2. Dilute the above solutions 50× with DMEM/10% FCS to obtain compound solutions 20× of the final concentrations.
3. Fill each lower chamber of a Fluoroblock 96-Muntiwell Insert plate with 180 μl DMEM/10% FCS, and plate 8,000 HPAF pancreatic cancer cells in 50 ul DMEM/10% FCS in each upper chamber.
4. 1-2 hours after plating, add 2.5 μl and 10 μl of a 20× compound solution to the upper and the lower chamber respectively. Incubate the plate at 37° C. for 60 min, and then add concentrated HGF to lower chamber to a final HGF concentration of 15 ng/ml. The insert plates are incubated overnight for 20 hours.
5. An aliquot of a concentrated Calcein dye (Molecular Probes) is added to each lower chamber to give 5 μg/ml final dye concentration and the cells are labeled for 1 hour. Wash each lower chamber with 200 μl DMEM/10% FCS
6. Read fluorescence on a Victor reader (PerkinElmer) in bottom read mode (Excitation wave length: 485 nm, emission wavelength: 535 nm).
7. $IC_{50}$ is calculated by fitting the relationship between compound concentration and fluorescence signal with a 4-parameter logistic equation.

V. In Vivo Bioavailability Assay
1. Rat:
Male Sprague-Dawley rats (n=4) weighing approximately 260-280 g are used for the pharmacokinetic (PK) studies. A cannula was implanted in the jugular vein for dose administration and blood sampling. For the intravenous leg of the study, the compound is administered as a bolus via the jugular vein at 2 mg/kg (12 mg/m², 0.4 mL/kg) in saline. Blood samples are serially collected predose, and at 0.033, 0.083, 0.25, 0.5, 1, 2, 4, 6, 8, and 24 hr following dose administration. For the oral leg of the study, the compound is administered by gavage at 5 mg/kg (30 mg/m²; 5 mL/kg) in 0.5% methylcellulose. Blood samples are serially collected predose, and at 0.25, 0.5, 1, 2, 4, 6, 8, and 24 hr following dose administration.
2. Dog.
Male Beagle dogs (n=4) weighing 7.7-8.5 kg are used for the PK studies. For the intravenous leg of the study, the compound is administered as a slow bolus via the cephalic vein at 1 mg/kg (20 mg/M2, 0.4 mL/kg) in saline. Blood samples are serially collected predose from the jugular vein, and at 0.033, 0.083, 0.25, 0.5, 1, 2, 4, 6, 8, 10, and 24 hr following dose administration. For the oral leg of the study, the compound is administered by gavage at 2 mg/kg (40 mg/m², 5 mL/kg) in 0.5% methylcellulose. Blood samples are serially collected predose, and at 0.25, 0.5, 1, 2, 4, 6, 8, 10, and 24 hr following dose administration (Notebook/Pages: 255273/1, 2; 255286/1, 2).

Plasma samples are stored at −70° C. immediately after collection until analysis.

B. Analytical Procedures

1. Determination of Compound 1 Levels in Plasma

The concentrations of the compound in rat and dog plasma is determined by a validated LC-MS/MS assay following a protein precipitation step. Internal standard (N-(5-oxo-3-phenyl-5H-benzo[4,5]cyclohepta[1,2-b]pyridin-7-yl)methanesulfonamide) is added to 100 µL aliquots of plasma samples, and proteins are precipitated by addition of two volumes of acetonitrile containing 0.1% formic acid followed by centrifugation at 4,000 rpm for 10 min. The supernatant is diluted with two volumes of 40% acetonitrile in water containing 0.1% formic acid. Samples are vortex-mixed and centrifuged for 5 min at 3,000 rpm and 20 µL of the supernatant is injected for analysis. LC-MS/MS analysis is done using Flux Rheos-2000 Pump interfaced to the API-4000 (MDS Sciex) mass spectrometer utilizing Heated Nebulizer interface. Separation is performed using a Supelco Discovery C18 column (50×2.1 mm, 5µ) and mobile phase consisting of water containing 0.1% formic acid (solvent A) and acetonitrile with 0.1% formic acid (solvent B), at a flow rate of 0.75 mL/min. The gradient started at 100% A for 1 min and is then increased to 100% B over 2 min. The gradient is maintained at 100% B for 1 min following which mobile phase is returned to initial conditions and the column is equilibrated for 1.5 min prior to the next injection. The total run time is 6 min. Quantitation is done by monitoring transitions of m/z 496.3 to m/z 365.2 for MK-2461 and m/z 377.2 to m/z 298.5 for internal standard. The method is linear across the concentration range of 2 to 2,000 ng/mL in plasma samples from both species. The inter-batch accuracy for QC samples should be within the range of 91.7 to 106.5% and 101.2 to 116.6% for rat and dog plasma samples, respectively.

2. Pharmacokinetic Analysis

Pharmacokinetic parameters are obtained using non-compartmental methods (Watson®). The area under the plasma concentration-time curve ($AUC_{0-t}$) is calculated from the first time point (0 min) up to the last time point with measurable drug concentration using the linear trapezoidal or linear/log-linear trapezoidal rule. The remaining area under the plasma concentration-time curve ($AUC_{t-inf}$) is estimated by dividing the observed concentration at the last time point by the elimination rate constant. This value is added to $AUC_{0-t}$ to estimate the $AUC_{0-inf}$. The percentage AUC extrapolated is a function of ($AUC_{0-inf}$-$AUC_{0-t}$) 100/$AUC_{0-inf}$. The IV plasma clearance is calculated by dividing the dose by $AUC_{0-inf}$. The terminal half-life of elimination is determined by unweighted linear regression analysis of the log-transformed data. The time points for determination of half-life are selected by visual inspection of the data. The volume of distribution at steady state ($Vd_{ss}$) is obtained from the product of plasma clearance and mean residence time (determined by dividing the area under the first moment curve by the area under the curve). The maximum plasma concentration ($C_{max}$) and the time at which maximum concentration occurred ($T_{max}$) are obtained by inspection of the plasma concentration-time data. Absolute oral bioavailability is determined from dose-adjusted IV and P.O. ($AUC_{0-inf}$) ratios.

EXAMPLES

Examples provided are intended to assist in a further understanding of the invention. Particular materials employed, species and conditions are intended to be illustrative of the invention and not limiting of the reasonable scope thereof.

Example 1

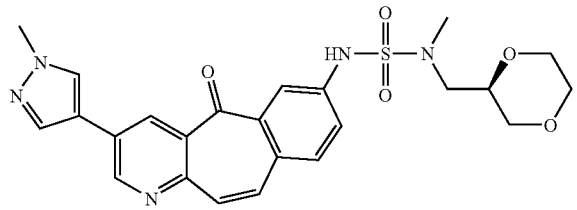

N-[(2R)-1,4-dioxan-2-ylmethyl]-N-methyl-NM-[3-(1-methyl-1H-pyrazol-4-yl)-5-oxo-5H-benzo[4,5]cyclohepta[1,2-b]pyridin-7-yl]sulfamide (Compound 1)

Step 1: 2-[(E/Z)-2-(4-bromophenyl)vinyl]-3-carboxy-5-chloropyridinium chloride

Potassium tert-butoxide (1 M solution in THF, 60 mL, 60 mmol) was added to a solution of 4-bromobenzaldehyde (5.6 g, 30 mmol) and methyl 5-chloro-2-methylnicotinate (Marcoux, J.-F.; Marcotte, F.-A.; Wu, J.; Dormer, P. G.; Davies, I. W.; Hughes, D.; Reider, P. J. *J. Org. Chem.* 2001, 66, 4194-4199) (5.6 g, 30 mmol) in 200 mL THF at 0° C. The mixture was allowed to warm to ambient temperature and stirred for 12 hours. The reaction slurry was concentrated to give yellow/orange solids, then 50 mL of water and 50 mL of 6N HCl were added. After stirring the resulting slurry for 30 minutes, 200 mL of EtOH was added and the slurry was stirred for 4 hours. The slurry was filtered and dried to afford the title compound. ¹H NMR (600 MHz, DMSO-D₆) δ 8.76 (d, 1H); 8.22 (d, 1H); 8.02 (d, 1H); 7.79 (d, 1H); 7.60-7.54 (m, 4H). LRMS (APCI) calculated for $C_{14}H_{10}BrClNO_2$ [M+H]+, 338.0; found 337.9.

Alternate Step 1: 2-[(E)-2-(4-Bromophenyl)vinyl]-5-chloronicotinic Acid

A stirred solution of methyl 5-chloro-2-methylnicotinate (7.26 kg, 96.4 wt %, 37.7 mol) and 4-bromobenzaldehyde (6.98 kg, 37.7 mol, 1.0 equiv) in THF (112 L) was put under a nitrogen atmosphere, and then cooled to −5° C. A solution of potassium tert-butoxide (8.46 kg, 75.4 mol, 2.0 equiv) in THF (53 L) was then added via a 1 µm filter, whilst maintaining the internal temperature at <0° C. The resulting reaction mixture was warmed to 25° C., and then aged at this temperature until the reaction was complete (typically 1 h). The reaction was then quenched by addition of water (54 L), ensuring the batch temperature remained <30° C. The biphasic mixture was stirred for ~10 min, and the lower aqueous layer was then removed. The remaining THF layer was diluted with ethyl acetate (54 L), and then washed with 2 M hydrochloric acid (27 L) followed by half-saturated brine (20 L). The resulting organic layer was solvent-switched to ethyl acetate (to a final volume of 27 L), and then to methanol (to give a final volume of ~106 L). The temperature of the resulting slurry was adjusted to ~20° C., and it was then filtered, washing the filter-cake with methanol (11 L). The resulting solid was dried under vacuum at 50° C. to afford the title compound.

Step 2: 7-bromo-3-chloro-5H-benzo[4,5]cyclohenta [1,2-b]pyridin-5-one

2-[(E/Z)-2-(4-bromophenyl)vinyl]-3-carboxy-5-chloropyridinium chloride (11.2 g, 29.9 mmol) was added to 50 mL of polyphosphoric acid and heated to 200° C. After 12 hours, the solution was poured into ice and 250 mL of 5 N sodium hydroxide solution, then SN sodium hydroxide solution was added to adjust to pH 10. The mixture was diluted in 2 L of dichloromethane, 100 g of Celite were added and the suspension was stirred for 15 minutes. The solids were filtered through a sintered glass funnel and discarded. The liquid phase was poured into a separatory funnel and the organic layer was isolated. The organic layer was dried with magnesium sulfate, filtered, and concentrated to afford the title compound. $^1$H NMR (600 MHz, CDCl$_3$) δ 8.82 (d, 1H); 8.50 (d, 1H); 8.41 (d, 1H); 7.80 (dd, 1H); 7.48 (d, 1H); 7.35 (d, 1H); 7.20 (d, 1H). LRMS (APCI) calculated for $C_{14}H_8BrClNO$ [M+H]+, 320.0; found 320.0.

Alternate Step 2: 7-Bromo-3-chloro-5H-benzo[4,5] cyclohenta[1,2-b]pyridin-5-one

Polyphosphoric acid (72 kg) was heated to ~180° C. (internal temperature) under a nitrogen atmosphere. 2-[(E)-2-(4-Bromophenyl)vinyl]-5-chloronicotinic acid (7.2 kg, 93.1 wt %, 19.8 mol) was then added to the stirred polyphosphoric acid, and the resulting reaction mixture was heated to 215° C. (internal temperature). The resulting mixture was then aged at this temperature (210-220° C.) until the reaction was complete (typically 4 h). The reaction mixture was then allowed to cool to 90° C., and water (94 L) was carefully added to the stirred batch at a rate sufficient to maintain the internal temperature at 80-100° C. Once this addition was complete, the batch was allowed to cool to ambient temperature. Acetonitrile (145 L) was then added over a period of ~1 h, and the resulting slurry was filtered, washing the wet-cake with acetonitrile (36 L). The solid collected was dried, and then dissolved in dichloromethane (231 L) containing triethylamine (3.4 kg). Ecosorb C-941 (0.9 kg) was added, and the batch was left to stir for 1 h before filtering, washing the filter pad twice with dichloromethane (2×22 L). The combined filtrate and washes were then solvent-switched to acetonitrile (to a final volume of 120 L), under atmospheric pressure. The resulting slurry was cooled to 20° C., aged at this temperature overnight, and then filtered, washing the wet-cake three times with acetonitrile (3×29 L). The resulting filter-cake was dried to afford crude title compound.

Step 3: Benzyl (1,4-dioxan-2-ylmethyl)methylcarbamate 1-(1,4-dioxan-2-yl)-N-methylmethanamine hydrochloride (4.83 g, 29 mmol) was dissolved in 100 mL dichloromethane. Benzyl chloridocarbonate (4.9 mL, 35 mmol) and triethylamine (10 mL, 72 mmol) were added. The solution was stirred at ambient temperature. After 12 hours, the solution was concentrated, then diluted with ethyl acetate, and washed with saturated sodium bicarbonate and water. The organic layer was separated, dried with magnesium sulfate, filtered, concentrated in vacuo, and purified by silica chromatography (0-100% ethyl acetate/hexanes gradient) to afford the title compound (racemic mixture).

The racemic mixture (6.35 g) was dissolved in 24 mL heptane and 8 mL isopropanol. Material was resolved on chiral AD column (15% isopropanol/heptane) to afford 2.9 g enantiomer A [$\tau_R$: 9.43 min (analytical chiral HPLC, AD column, 0.46 cm×25 cm cm id, 15% isopropanol/heptane, isocratic, flow rate=0.75 mL/min)] and 2.9 g enantiomer B [$\tau_R$: 10.92 min (analytical chiral HPLC, AD column, 0.46 cm×25 cm cm id, 15% isopropanol/heptane, isocratic, flow rate=0.75 mL/min)]. LRMS (APCI) calc'd for ($C_{14}H_{20}NO_4$) [M+H]+, 266.1; found, 266.2.

Step 4: 1-(1,4-dioxan-2-yl)-N-methylmethanamine hydrochloride

Benzyl (1,4-dioxan-2-ylmethyl)methylcarbamate (Enantiomer A, 2.9 g, 10.9 mmol) was dissolved in 50 mL dry ethanol. 10% (w/w) palladium on carbon (0.29 g) and 1.0 mL 10 N HCl were added. The flask was sealed and flushed with hydrogen. Stirred solution under a hydrogen balloon. After 12 hours, the solution was filtered through celite and concentrated in vacuo to afford the title compound. $^1$H NMR (600 MHz, D$^6$-DMSO) δ8.64 (s, 2H); 3.82-3.75 (m, 2H); 3.69 (d, 1H); 3.64 (d, 1H); 3.59 (m, 1H); 3.44 (m, 1H); 3.22 (t, 1H); 2.94-2.84 (m, 2H); 2.51 (s, 3H).

Step 5: tert-butyl {[((2R)-1,4-dioxan-2-ylmethyl) (methyl)amino]sulfonyl}carbamate 1-(1,4-dioxan-2-yl)-N-methylmethanamine hydrochloride (0.760 g, 4.55 mmol), N-[1-{[(tert-butoxycarbonyl) amino]sulfonyl}pyridin-4(1H)-ylidene]-N-methylmethanaminium (1.51 g, 5.00 mmol), and triethylamine (1.55 mL, 11.4 mmol) were slurried in 50 mL dichloromethane and stirred at ambient temperature. After 12 hours, the solution was concentrated in vacuo and purified by silica chromatography (50-100% ethyl acetate/hexanes gradient) to afford the title compound. LRMS (APCI) calc'd for ($C_{11}H_{22}N_2O_6SNa$) [M+Na]+, 333.1; found, 333.1.

Step 6: {[((2R) 1,4-dioxan-2-ylmethyl)(methyl) amino]sulfonyl}ammonium trifluoroacetate tert-butyl {[(1,4-dioxan-2-ylmethyl)(methyl)amino] sulfonyl}carbamate (1.25 g, 4.03 mmol) was dissolved in 10 mL dichloromethane and 20 mL trifluoroacetic acid and stirred at ambient temperature. After 2 hours, the solution was concentrated and azeotroped twice with heptane to afford the title compound. LRMS (APCI) calc'd for ($C_6H_{15}N_2O_4S$) [M+H]+, 211.1; found, 211.1.

Step 7: N'-(3-chloro-5-oxo-5H-benzo[4,5]cyclohepta [1,2-b]pyridin-7-yl)-N-[(2R)-1,4-dioxan-2-ylmethyl]-N-methylsulfamide 7-bromo-3-chloro-5H-benzo[4,5]cyclohepta[1,2-b]pyridin-5-one (1.41 g, 4.41 mmol), {[((2R) 1,4-dioxan-2-ylmethyl)(methyl)amino]sulfonyl}ammonium trifluoroacetate (1.30 g, 4.01 mmol), tris(dibenzylideneacetone)dipalladium (0.183 g, 0.20 mmol), 9,9-dimethyl-4,5-bis(diphenylphosphino)xanthene (0.347 g, 0.60 mmol), and cesium carbonate (3.91 g, 12.0 mmol) were combined in a dry flask. 50 mL dry dioxane was added and argon was bubbled through the solution for five minutes. The solution was stirred and heated to 95° C. After 2 hours, the solution was concentrated in vacuo, diluted with ethyl acetate, and washed with water and brine. The organic layer was isolated, dried with magnesium sulfate, filtered, concentrated in vacuo, and purified by silica chromatography (0-100% ethyl acetate/hexanes gradient) to afford the title compound. LRMS (APCI) calc'd for ($C_{20}H_{21}ClN_3O_5S$) [M+H]+, 450.1; found, 450.1.

Alternate Step 7: N'-(3-chloro-5-oxo-5H-benzo[4,5]cyclohepta[1,2-b]pyridin-7-yl)-N-[(2R)-1,4-dioxan-2-ylmethyl]-N-methylsulfamide A stirred solution of 7-bromo-3-chloro-5H-benzo[4,5]cyclohepta[1,2-b]pyridin-5-one (10 g, 1.0 equiv), {[((2R)1,4-dioxan-2-ylmethyl)(methyl)amino]-sulfonyl}amine (6.9 g, 1.05 equiv), sodium tert-butoxide (6.6 g, 2.2 equiv), $Pd_2(dba)_3$ (0.29 g, 0.01 equiv), and Xantphos (0.36 g, 0.02 equiv) in toluene (250 mL) was thoroughly de-gassed, and then put under a nitrogen atmosphere. The resulting reaction mixture was then heated to 60° C., and left to age at this temperature until the reaction was complete (typically 1.5 h). The batch was then cooled to ambient temperature, and water (150 mL) was added. The resulting biphasic mixture was allowed to settle, and the aqueous layer was collected. The organic layer was extracted with 0.2 M aqueous NaOH (150 mL), the aqueous layers were combined and then washed twice with DCM (100 mL, then 50 mL). To the resulting aqueous layer was added DCM (200 mL) followed by concentrated hydrochloric acid (~10 mL). After mixing thoroughly, the two layers were separated and the aqueous layer was extracted twice with DCM (100 mL, then 50 mL). The combined DCM layers were washed with water (100 mL), and then solvent-switched into toluene (to a final volume of ~150 mL). The resulting slurry was aged at ~20° C. for at least 1 h and then filtered, washing the filter-cake with toluene (30 mL, then 20 mL). The resulting solid was dried under vacuum at 40° C. to afford the title compound.

Step 8: (2S)-2-[(benzyloxy)methyl]-1,4-dioxane (2R)-3-(benzyloxy)propane-1,2-diol (2.00 g, 11.0 mmol) and tetrabutylammonium bromide (708 mg, 2.20 mmol) were dissolved in 50 mL of 1,2-dichloroethane, then 50 mL of a 50% (w/w) aqueous sodium hydroxide solution was added quickly and the mixture was heated to 50° C. After 18 h, an additional 50 mL of 1,2-dichloroethane and 50 mL of 50% (w/w) sodium hydroxide solution was added. After 8 h, additional 50 mL of 1,2-dichloroethane was added. After 72 h, the mixture was diluted in diethyl ether, washed with water and brine, then dried over sodium sulfate and concentrated. The residue was purified by flash column chromatography (silica, ethylacetate/hexanes) to afford the title compound. $^1$H NMR (600 MHz, $CDCl_3$) δ 7.26-7.35 (m, 5H); 4.51-4.56 (m, 2H); 3.72-3.82 (m, 4H); 3.67-3.71 (m, 1H); 3.58-3.64 (m, 1H); 3.38-3.48 (m, 3H).

Step 9: benzyl[(2S)-1,4-dioxan-2-ylmethyl]methylcarbamate

A round bottomed flask was charged with (2S)-2-[(benzyloxy)methyl]-1,4-dioxane (1.77 g, 8.48 mmol), 902 mg of 10% Pd/C and 50 mL of absolute ethanol. A three-way stopcock fitted with a hydrogen balloon was affixed to the flask, then the flask was evaporated and back-filled with hydrogen (4×) and stirred under the hydrogen atmosphere overnight. The mixture was filtered through Celite and concentrated to afford (2S)-1,4-dioxan-2-ylmethanol.

A round bottomed flask was charged with (2S)-1,4-dioxan-2-ylmethanol (115 mg, 0.973 mmol), triethylamine (0.204 mL, 1.46 mmol), and 5 mL of dichloromethane then cooled to –10° C. Methanesulfonyl chloride (91 μL, 1.17 mmol) was added by syringe and the solution was stirred for 30 minutes at –10° C. The solution was diluted in dichloromethane, washed with 1 M HCl, and the aqueous layer was extracted with dichloromethane (2×). The combined organic layers were washed with saturated aquoues sodium bicarbonate (2×) and brine, then dried over sodium sulfate and concentrated to afford (2R)-1,4-dioxan-2-ylmethyl methanesulfonate.

Sodium hydride (29 mg, 0.74 mmol) was suspended in 2 mL of N,N-dimethylformamide (DMF) and cooled to 0° C. A solution of benzyl methylcarbamate (81 mg, 0.49 mmol) in 2 mL of DMF was added via syringe. After 20 minutes, a solution of (2R)-1,4-dioxan-2-ylmethyl methanesulfonate (191 mg, 0.97 mmol) in 2 mL of DMF was added by syringe and the mixture was heated to 70° C. After 2 h the mixture was cooled to ambient temperature, then diluted in diethyl ether, washed with water and brine, then dried over sodium sulfate and concentrated. The residue was purified by flash column chromatography (silica, ethylacetate/hexanes) to afford the title compound. LRMS (APCI) calc'd for ($C_{14}H_{20}NO_4$) [M+H]+, 266.1; found, 266.2.

Analysis of benzyl[(2S)-1,4-dioxan-2-ylmethyl]methylcarbamate by analytical HPLC [$\tau_R$: 10.85 min (analytical chiral HPLC, AD column, 0.46 cm×25 cm id, 15% isopropanol/heptane, isocratic, flow rate=0.75 mL/min)] and co-injection with Enantiomer A from Step 3 allowed for the following assignment of stereochemistry for the separated enantiomers of Step 3.

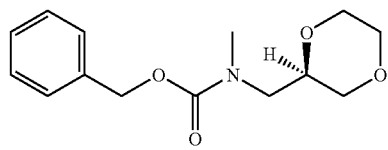

Enantiomer A

Benzyl[(2R)-1,4-dioxan-2-ylmethyl]methylcarbamate

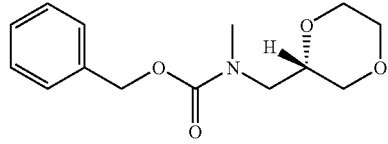

Enantiomer B

Benzyl[(2S)-1,4-dioxan-2-ylmethyl]methylcarbamate

Step 10: N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide (Compound 1)

N'-(3-chloro-5-oxo-5H-benzo[4,5]cyclohepta[1,2-b]pyridin-7-yl)-N-[(2R) 1,4-dioxan-2-ylmethyl]-N-methylsulfa mide (0.500 g, 1.11 mmol), 1-methyl-4-(4,4,5,5-tetramethyl-1,3,2-dioxaborolan-2-yl)-1H-pyrazole (0.692 g, 3.33 mmol), Pd$_2$(dba)$_3$ (0.051 g, 0.056 mmol), (tBu$_3$)PBF$_4$ (0.032 g, 0.11 mmol) and potassium fluoride (0.212 g, 3.66 mmol) were combined in a dry tube. 5 mL dry DMF was added and argon was bubbled through the solution for five minutes. The tube was sealed and heated in the Biotage Initiator series microwave to 135° C. for 20 minutes. The solution was diluted with ethyl acetate and washed with saturated sodium bicarbonate, water, and brine. The organic layer was dried with magnesium sulfate, filtered, concentrated in vacuo, and purified by silica chromatography (0-100% ethyl acetate/hexanes gradient followed by 0-10% methanol/dichloromethane gradient) to afford the crude compound. The crude material was crystallized from a mixture of 10 mL methanol, 40 mL dichloromethane, and 70 mL hexanes to afford the title compound. $^1$H NMR (600 MHz, D$^6$-DMSO) δ 10.52 (s, 1H); 9.20 (d, 1H); 8.55 (d, 1H); 8.45 (s, 1H); 8.13 (s, 1H); 7.95 (d, 1H); 7.75 (d, 1H); 7.55 (d, 1H); 7.32 (d, 1H); 7.22 (d, 1H); 3.88 (s, 3H); 3.64-3.60 (m, 2H); 3.58-3.54 (m, 1H); 3.54-3.50 (m, 1H); 3.44-3.40 (m, 1H); 3.38-3.34 (m, 1H); 3.14-3.10 (m, 3H); 2.77 (s, 3H). LRMS (APCI) calc'd for (C$_{24}$H$_{26}$N$_5$O$_5$S) [M+H]+, 496.2; found, 496.2.

Alternate Step 10: N-[(2R)-1,4-dioxan-2-ylmethyl]-N-methyl-N'-13-(1-methyl-1H-pyrazol-4-yl)-5-oxo-5H-benzo[4,5]cyclohepta[1,2-b]pyridin-7-yl]sulfamide (Compound 1)

ambient temperature for ~1 h and then filtered through Solka Floc. The filtrate was acidified by addition of 2 M hydrochloric acid (83 mL), and the resulting slurry was diluted with 2:1 DMF/water (150 mL). After aging overnight, the slurry was filtered, washing the filter-cake with 1:1 DMF/water (10 mL), and then three times with water (3×20 mL). The resulting solid was dried under vacuum at 50° C. to afford the title compound.

Example 1B

Enantioselective Synthesis of {[((2R)1,4-dioxan-2-ylmethyl)(methyl)amino]-sulfonyl}amine Step 1: Epoxide 1B-1

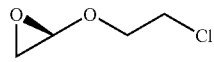

A solution of chloroethanol (13.0 kg, 10.9 L, 162 mole, 3 eq) and BF$_3$.OEt$_2$ (342 mL, 2.7 mol, 0.05 eq) in toluene (20 L)

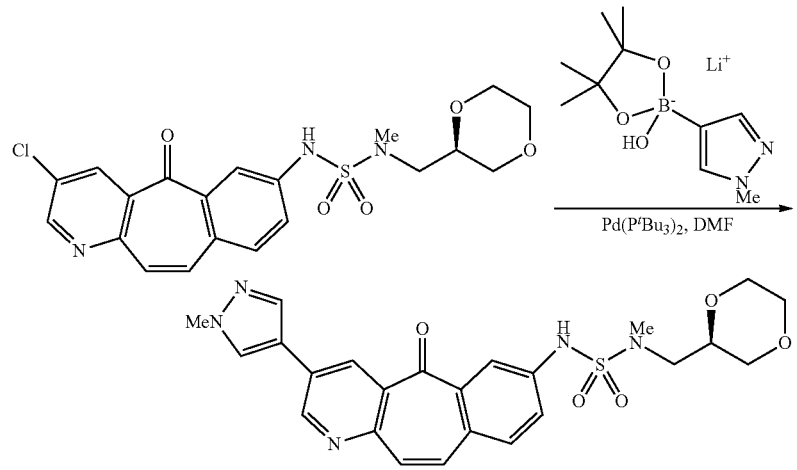

A mixture of N'-(3-chloro-5-oxo-5H-benzo[4,5]cyclohepta[1,2-b]pyridin-7-yl)-N-[(2R)1,4-dioxan-2-ylmethyl]-N-methylsulfamide (10 g, 21.9 mmol), 1-methyl-4-(4,4,5,5-tetramethyl-1,3,2-dioxaborolan-2-yl)-1H-pyrazole lithium hydroxyl-ate complex (10.7 g, 78 wt %, 35.9 mmol, 1.6 equiv) and bis(tri-tert-butylphosphine)palladium (67 mg, 0.13 mmol, 0.006 eq) in DMF (100 mL) was thoroughly de-gassed, and then put under a nitrogen atmosphere. The reaction mixture was then heated to 100° C., and left to age at this temperature until the reaction was complete (typically 1 h). The resulting reaction mixture was cooled to ambient temperature and 2 M NaOH (50 mL) was then added, followed by Ecosorb C-941 (1.0 g). The mixture was stirred at was heated to an internal temp of 36° C. and S-epichlorohydrin added dropwise with cooling at a rate such that the internal temperature remained below 38° C. In 30 min after completion of the addition the reaction was completed. The mixture was cooled to 10° C. and sodium hydroxide (12.5 L) and water (12.5 L) were added. The bi-phasic mixture was stirred at room temperature for 2 hours and a further 10 L of water was added to dissolve the inorganic solids. The layers were separated and the aqueous layer was extracted with toluene (20 L). The combined organic layers were washed with water (15 L) and then concentrated to an approximately 50 wt % of product in toluene solution. The resulting viscous solution was used directly in the following reaction.

Step 2: Tosylate 1B-2

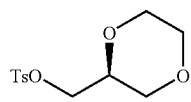

A solution of conc. aqueous NaOH solution (26.1 L) and water (31.3 L) was heated to 87° C. Crude epoxide 1B-1 (prepared as above; 5.24 kg, 38.4 mol) was added and the reaction aged at 90° C. for 30 min. The reaction was cooled to 22° C. and then diluted with DCM (21 L). p-Toluenesulfonyl chloride (7.46 kg, 38.36 mol) was added and the mixture was aged at 22° C. for 16 h. Water (21 L) was added and the phases separated. The aqueous layer was extracted with DCM (2×21 L). The combined organic layers were washed with a 5% brine solution (21 L). The organic layer was concentrated in vacuo and the residue dissolved in toluene (32 L). Heptane (7 L) was added followed by 22B-2 as seed (100 g) and the mixture cooled to 4° C. After ageing for 16 h, the mixture was filtered and the solids washed with 8:1 heptane/toluene (4 L). Tosylate 1B-2 was isolated as a white solid:

$^1$H NMR (CDCl$_3$) δ 2.47 (3H, s), 3.37 (1H, dd, J=9.6, 11.2 Hz), 3.70 (6H, m), 3.97 (1H, dd, J=4.8, 10.4 Hz), 4.03 (1H, dd, J=5.4, 10.6 Hz), 7.37 (2H, d, J=8.1 Hz), 7.81 (2H, d, J=8.3 Hz).

Step 3: 1-(1,4-dioxan-2-yl)-N-methylmethanamine hydrochloride

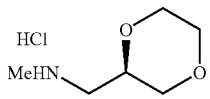

A solution of tosylate 1B-2 (7.76 kg), methylamine in ethanol (62 L of a 33 wt % solution) and ethanol (62 L) was heated to an internal temperature of 65° C. for 20 h. The resulting solution was then concentrated via atmospheric distillation to a volume of 15 L. This solution was held at 50° C. while NaOEt (9.2 L of a 21 wt % solution in ethanol; 1.05 equiv) was added, along with MTBE (47 L) each in two alternating portions. The slurry was then cooled to room temperature and filtered to remove sodium tosylate. The solids were washed with MTBE (15.5 L). The combined filtrates were solvent switched to isopropanol via atmospheric distillation. The final volume was ~30 L. Conc. HCl (2.1 L of S.G. 1.18, 1.05 equiv) was added whilst keeping the temperature <60° C. Isopropanol (116 L) was added, and the batch was concentrated via atmospheric distillation to a total volume of ~30 L. This mixture was held at 50° C. until a slurry formed, then cooled to room temperature overnight. The solids were filtered, washed with 1:1 heptane:isopropanol (15 L) and dried to give 1B-3 as a white solid.

$^1$H NMR (400 MHz, MeOD): δ 3.90 (m, 2H), 3.77 (m, 3H), 3.62 (tr d, J=12 Hz, J=2.5 Hz, 1H), 3.36 (m, 1H), 3.06 (m, 2H), 2.73 (s, 3H)

Step 4: {[((2R)1,4-dioxan-2-ylmethyl)(methyl)amino]-sulfonyl}amine

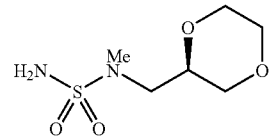

To a cold (−20° C.) solution of chlorosulfonylisocyanate (2954 g) in dichloromethane (12.6 L) was added benzyl alcohol (2438 g) over 50 min, keeping the temperature below 0° C. A solution of 1B-3 free base was prepared by stirring 1B-3 (2795 g) with diisopropylethylamine (8.63 kg) in dichloromethane (33.5 L) for 1 h. This was then added to the sulfamoylating reagent over 100 min, keeping the temperature below 0° C. After 45 min, the batch was quenched by the addition of 4M HCl (13 kg) whilst keeping the temperature <5° C. The phases were separated and the DCM layer was washed with water (18.6 kg) and then solvent switched to methanol and a final volume of 106 L was reached. This solution was hydrogenated in the presence of 10% Pd/C (50% wet) (801 g) for 1 h at 1 bar of hydrogen. The catalyst was filtered and washed with methanol (2×20 L). The combined filtrates were solvent switched to isopropanol (final volume 32 L). A seed-bed formed. Heptane (72 L) was slowly added over 1 h. The slurry was aged for 1 h and then filtered, The solids were washed with 1:2 isopropanol:heptane (10 L) and dried to give 1B-4.

$^1$H NMR (400 MHz, MeOD): δ 3.79 (m, 3H), 3.71 (m, 2H), 3.59 (tr d, J=2.7 Hz, J=12 Hz, 1H), 3.36 (m, 1H), 3.10 (m, 2H), 2.85 (s, 3H).

Example 1C-1

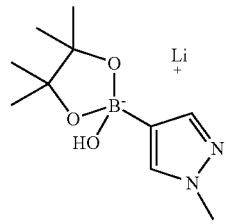

1-methyl-4-(4,4,5,5-tetramethyl-1,3,2-dioxaborolan-2-yl)-1H-pyrazole lithium hydroxyl-ate Complex 1C-1

A solution of 4-bromo-1-methylpyrazole (101 g, 96 wt % pure, 600 mmol) in THF (600 mL) and toluene (600 mL) was degassed three times by vacuum/nitrogen cycles and then left under an atmosphere of nitrogen. Triisopropyl borate (147 g, 181 mL, 1.3 equiv.) was added and the mixture was cooled to −74° C. A n-Hexyllithium solution (2.3 M in hexanes, 391 mL) was added slowly via canula over 90 min whilst maintaining the temperature <−67° C. The resulting viscous pink solution was aged for 15 min. Pinacol (106 g, 1.5 equiv.) was added and the mixture was warmed to +25° C. over 40 minutes. The mixture is aged for 80 min. Water (54 g, 5.0 equiv.) was added dropwise over 10 min to form a white slurry. The slurry was aged for 2.5 h at ambient temperature. The solids were filtered, washed with MTBE (2×250 mL) and dried in vacuo at 35° C. for 16 h. The intermediate IC-1 was obtained as a dry white solid.

Example 2

Preparation of Compound 1 Sodium Salt Dihydrate

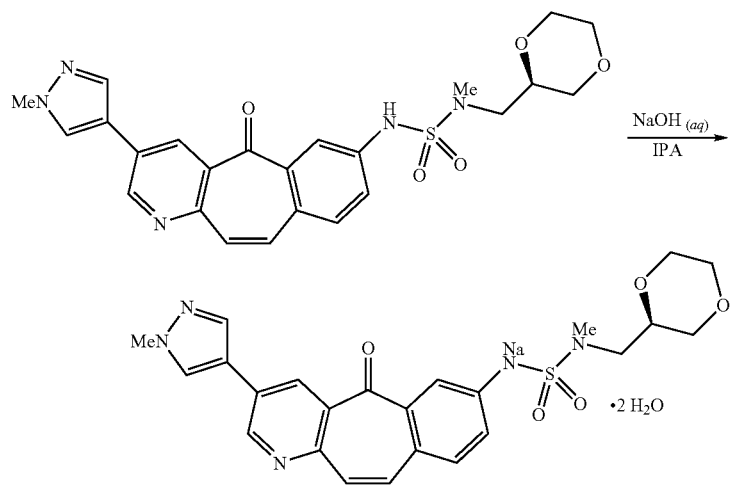

To a stirred suspension of Compound 1 (2.67 kg, 5.39 mol) in 4:1 propan-2-ol/water (13.5 L) was added 2 M aqueous NaOH (2.70 L, 5.40 mol). The resulting cloudy solution was then filtered, washing through with 4:1 propan-2-ol/water (2.5 L). The orange solution obtained was diluted with propan-2-ol (8 L), and the water content was then reduced to ~3.5% v/v by distillation at atmospheric pressure, whilst adding propan-2-ol (53.9 L added in total) to maintain a constant batch volume. Seed (25 g of Compound 1 sodium salt dihydrate) was added after ~50 L of solvent had been distilled off. Once the distillation was complete, the resulting stirred slurry was left to slowly cool to ambient temperature overnight. The yellow slurry was then filtered, washing the wet-cake twice with 2% v/v water in propan-2-ol (2×8.1 L). The resulting filter-cake was dried under vacuum at 35° C., for ~3 h, to afford Compound 1 sodium salt dihydrate as a yellow solid, which was crystalline by XRPD (see FIG. 1; Selected characteristic peaks positions are listed in Table 1). Karl Fisher analysis indicates water content consistent with a double hydrated form. $^1$H NMR (400 MHz, DMSO-$d_6$; water peak omitted): δ 9.13 (d, J=2.3 Hz, 1H), 8.55 (d, J=2.3 Hz, 1H), 8.43 (s, 1H), 8.10 (s, 1H), 7.72 (d, J=2.4 Hz, 1H), 7.40 (d, J=8.6 Hz, 1H), 7.29-7.20 (dd, J=8.6, 2.4 Hz, 1H), 7.21 (d, J=11.9 Hz, 1H), 6.99 (d, J=12.2 Hz, 1H), 3.90 (s, 3H), 3.68-3.59 (om, 3H), 3.56-3.45 (om, 2H), 3.43-3.31 (m, 1H), 3.11-3.01 (om, 2H), 2.78 (dd, J=13.7, 5.1 Hz, 1H), 2.59 (s, 3H).

The Compound 1 sodium salt dihydrate is chemically and physically stable for 6 Months at 40° C./75% relative humidity (RH).

X-ray powder diffraction data of the sodium salt dihydrate was collected on a Bruker D8 Advance X-ray powder diffractometer in the Bragg-Brentano (theta-theta) geometry with a 435 mm measuring circle. The X-ray source used copper radiation Kα1 and Kα2, with a tube power of 1600 W (40 kV and 40 mA). A Position Sensitive Detector was used to acquire the data. All diffractograms were acquired with a 2θ range of 3-40° with no prior sample preparation. The Diffraction spectrum is shown in FIG. 1 and selected peaks are listed in Table 1.

TABLE 1

Characteristic sodium salt dihydrate XRPD peaks.

| Intensity | Angle 2-Theta ° |
|---|---|
| v. strong | 6.9 |
| strong | 13.9 |
| medium | 15.6 |
| medium | 17.7 |
| medium | 18.0 |
| medium | 21.8 |
| medium | 22.0 |
| medium | 22.9 |
| medium | 25.7 |

Peaks are referenced to the silicon peak at 28.443 2-Theta°.

Example 3

Preparation of Compound 1 Potassium Salt Monohydrate

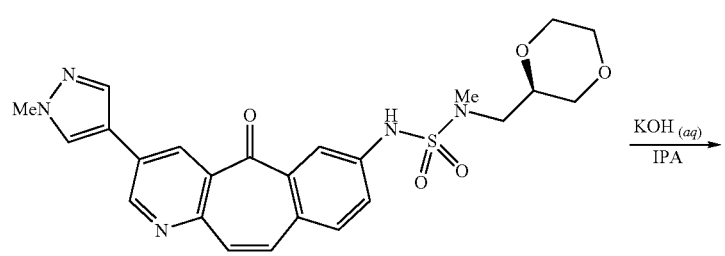

-continued

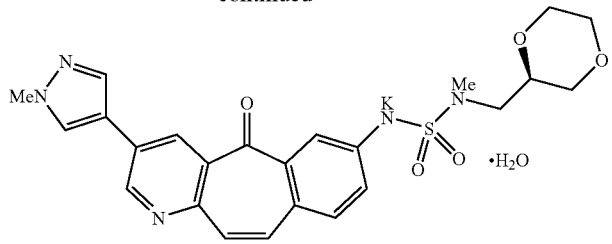

A stirred suspension of Compound 1 (500 mg, 1.01 mmol) in propan-2-ol (15 mL) was heated to 50° C. 1.75 M aqueous potassium hydroxide (0.577 mL, 1.01 mmol) was added over a period of 5 minutes. The resulting mixture was aged at 50° C. for 90 minutes, slowly cooled to room temperature over 4 hours, and then filtered. Compound 1 potassium salt monohydrate was isolated as a yellow solid, which was crystalline by XRPD (selected characteristic peaks positions are listed in Table 2). Karl Fisher analysis indicates water content consistent with a monohydrated form. $^1$H NMR (400 MHz, DMSO-$d_6$; water peak omitted): δ 9.12 (d, J=2.3 Hz, 1H); 8.55 (d, J=2.3 Hz, 1H); 8.43 (s, 1H); 8.10 (s, 1H); 7.70 (d, J=2.4 Hz, 1H); 7.39 (d, J=8.5 Hz, 1H); 7.22 (dd, J=8.5, 2.4 Hz, 1H); 7.20 (d, J=12.3 Hz, 1H); 6.98 (d, J=12.2 Hz, 1H); 3.90 (s, 3H); 3.67-3.57 (om, 3H); 3.57-3.45 (om, 2H); 3.41-3.33 (td, J=11.2, 3.0 Hz, 1H); 3.08 (dd, J=12.0, 10.2 Hz, 1H); 3.04 (dd, J=13.7, 7.0 Hz, 1H); 2.77 (dd, J=13.7, 4.9 Hz, 1H); 2.58 (s, 3H).

Figure 2:
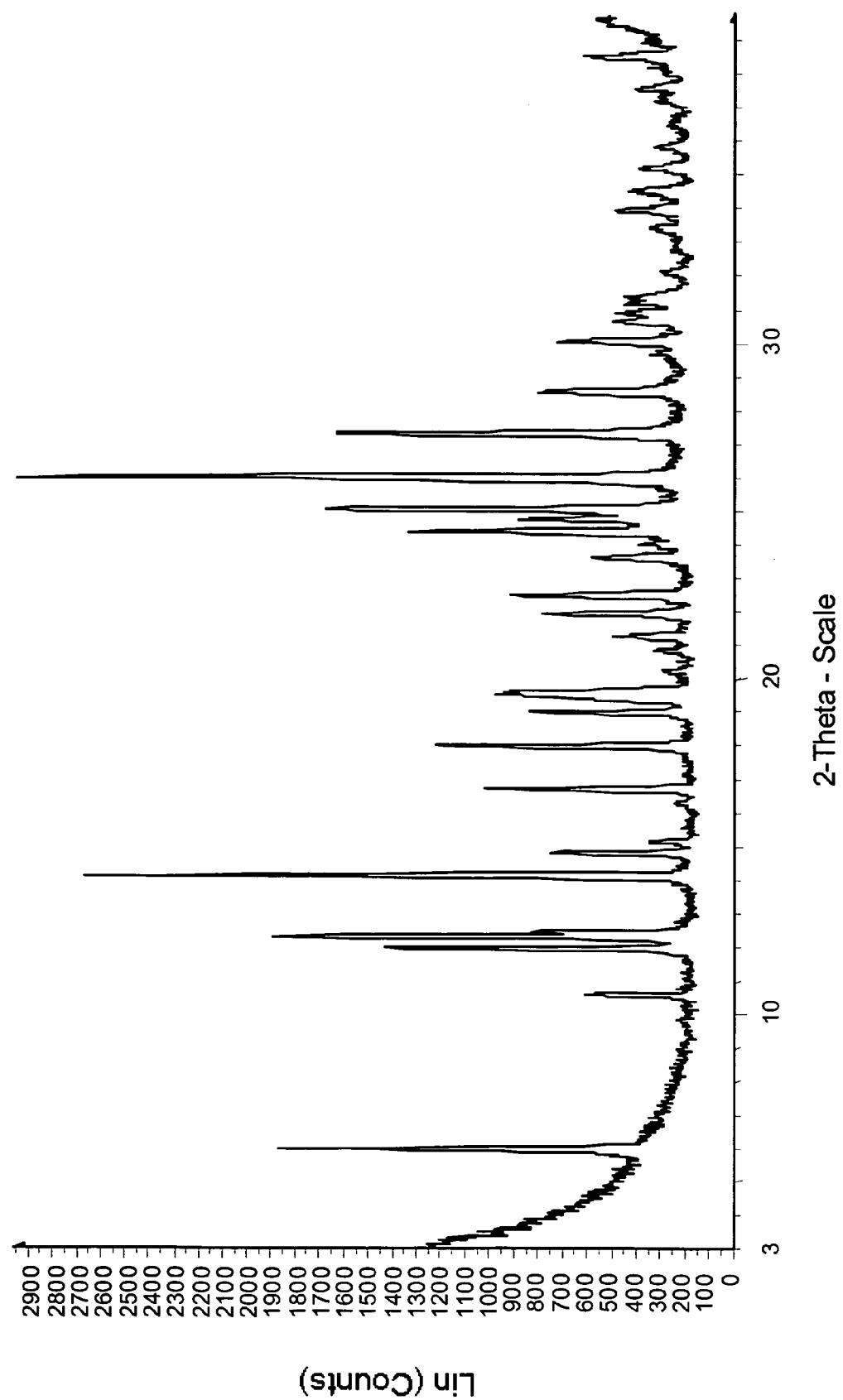
FIG. 2: The XRPD spectrum for N-[(2R)-1,4-dioxan-2-ylmethyl]-N-methyl-N'-[3-(1-methyl-1H-pyrazol-4-yl)-5- oxo-5H-benzo[4,5]cyclohepta[1,2-b]pyridin-7-yl]sulfamide potassium salt monohydrate is shown.

X-ray powder diffraction data of the potassium salt monohydrate was collected on collected on a Bruker D8 Advance X-ray powder diffractometer in the Bragg-Brentano (theta-theta) geometry with a 435 mm measuring circle. The X-ray source used copper radiation Kα1 and Kα2, with a tube power of 1600 W (40 kV and 40 mA). A Position Sensitive Detector was used to acquire the data. All diffractograms were acquired with a 2θ range of 3-40° with no prior sample preparation. The Diffraction spectrum is shown in FIG. 2 and selected characteristic peaks are listed in Table 2.

TABLE 2

Characteristic potassium salt monohydrate XRPD peaks.

| Intensity | Angle 2-Theta ° |
|---|---|
| strong | 6.0 |
| strong | 14.2 |
| medium | 16.8 |
| medium | 18.0 |
| medium | 19.1 |
| medium | 22.6 |
| strong | 25.1 |
| strong | 26.1 |
| strong | 27.4 |

Peaks are referenced to the silicon peak at 28.443 2-Theta°.

TABLE 3

Comparisons of the thermal analysis and solubility of the various salt forms of Compound 1:

| Salt | Crystal form | Thermal analysis (Melting/Crystal Change Onset,° C.) | Hygroscopicity (25° C.) | Solubility in water | Observed Polymorphism |
|---|---|---|---|---|---|
| Free Acid | Anhydrous | Onset 189.48° C. Peak 191.30° C. | 0.4% up to 80% RH | 0.003 mg/mL | 3 forms observed |
| Amorphous Sodium salt | NA | NA | 21% up to 80% RH | >400 mg/mL | NA |
| Crystalline Sodium salt | Double hydrated | Onset 110° C. Peak 141.2° C. | 0.14% up to 80% | >400 mg/mL Native pH = 10.5 | 1 transient solvate from MeOH swish converting into a metastable type A hydrate |
| Amorphous potassium salt | NA | NA | 30% up to 80% RH | >400 mg/mL | NA |
| Crystalline potassium salt | Mono hydrated | Onset approx. 146° C. Peak 175.5° C. | 0.81% up to 80% | >170 mg/mL Native pH = 10.7 | None observed |

The solubility of the hydrochloride salt of Compound 1 was also evaluated: 0.009 mg/ml (ph 2.6).

Additional Salt Forms of Compound 1

A different crystalline form of the sodium salt was obtained from aqueous NaOH in propan-2-ol using a similar procedure to that in Example 3 for the potassium salt monohydrate, except the mixture was cooled (over ~1 h) as soon as the base had been added.

A potential third crystalline form of the sodium salt was obtained by treating Compound 1 with NaOH in toluene, DME, or isopropyl acetate.

A crystalline choline [(2-hydroxyethyl)trimethylammonium] salt was obtained by treating Compound 1 with choline hydroxide in toluene or isopropyl acetate.

What is claimed is:

1. A compound selected from:

N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide sodium salt dihydrate; and N-[(2R)-1,4-dioxan-2-ylmethyl]-N-methyl-N'[3-(1-methyl-1H-pyrazol-4-yl)-5-oxo-5H-benzo[4,5]cyclohepta[1,2-b]pyridin-7-yl]sulfamide potassium salt monohydrate.

2. A pharmaceutical composition that is comprised of a compound in accordance with claim 1 and a pharmaceutically acceptable carrier.

* * * * *